United States Patent [19]

Jegelka et al.

[11] Patent Number: 5,945,536

[45] Date of Patent: Aug. 31, 1999

[54] CONTINUOUS PROCESS FOR PREPARING 4-AMINOPIPERIDINES

[75] Inventors: Udo Jegelka, Recklinghausen; Guenter Kreilkamp, Langehegge, both of Germany

[73] Assignee: Huels Atiengesellschaft, Marl, Germany

[21] Appl. No.: 09/017,710

[22] Filed: Feb. 5, 1998

[30] Foreign Application Priority Data

Feb. 6, 1997 [DE] Germany .............. 197 04 460

[51] Int. Cl.$^6$ .................................................. C07D 211/56
[52] U.S. Cl. ........................................... 546/244; 502/337
[58] Field of Search .............................. 546/244; 502/337

[56] References Cited

U.S. PATENT DOCUMENTS 5,773,622  6/1998  Jegelka et al. .................... 546/244

OTHER PUBLICATIONS

Chemical Abstract vol. 87 No. 135095, Kintopt et al, Redution of 4–oxopiperidine to 4–hydrogen piperidine, 1977.

*Primary Examiner*—John Kight
*Assistant Examiner*—Raymond Covington
*Attorney, Agent, or Firm*—Oblon, Spivak, McClelland, Maier & Neustadt, P.C.

[57] ABSTRACT

N-monosubstituted 4-aminopiperidine is prepared by a process comprising, in a single stage, continuously passing a 4-oxopiperidine and a primary amine over a metal hydrogenation catalyst under a hydrogen partial pressure of 1–500 bar at a LHSV of up to 1 hr$^{-1}$.

17 Claims, No Drawings

CONTINUOUS PROCESS FOR PREPARING 4-AMINOPIPERIDINES

BACKGROUND OF THE INVENTION

1. Field of the Invention

The present invention relates to a continuous process for preparing N-monosubstituted 4-aminopiperidines, which are primarily employed as starting materials for preparing sterically hindered amines which serve as stabilizers for synthetic polymers and are termed H.A.L.S. (hindered amine light stabilizers).

2. Description of the Background

The preparation of N-monosubstituted 4-aminopiperidines from the corresponding 4-oxopiperidines (or 4-piperidones), primary amines and hydrogen under hydrogenation conditions, that is by reductive amination, has long been known, and has been described, inter alia, in numerous patent publications. Hitherto, this process has been carried out in one stage, or, predominantly, in two stages, and, which is of importance for the present invention, always batchwise. A continuous process of production would be very desirable. Despite attempts of numerous research and development groups, however, it has not been possible to date to develop successfully a useful continuous process.

In the two-stage batchwise procedure, in the first stage, the Schiff's base is generated, which, after removal of the water of reaction, is then catalytically hydrogenated in the second stage to give the N-monosubstituted, that is secondary, amine. In the single-stage procedure, both reactions proceed simultaneously without removal of the water of reaction.

EP 0 354 184 describes the single- or two-stage reductive amination of triacetone amine derivatives with diamines in the presence of catalytic amounts of platinum, palladium or nickel. In the two-stage variant, water is removed by distillation azeotropically and the formation of the Schiff's base is thus forced. The single-stage procedure may only be carried out in the presence of acids as co-catalyst.

Although DE 3 007 996 describes the single-stage reductive amination of 4-piperidones with alkylamines or alkylenediamines in an inert solvent using Raney nickel or Raney cobalt as catalyst, the two-stage procedure using azeotropic removal of the reaction water, expediently with conjoint use of an ammonium salt as cocatalyst, is described as advantageous.

In the two-stage process disclosed in EP 0 033 663, various solvents are used in the two stages. In the first stage heptane is used, which at the same time functions as entrainer for the water of reaction, and in the hydrogenation stage isopropanol is used.

Clearly, it would be desirable if N-monosubstituted 4-aminopiperidines could be prepared with the same success, or even better, in only one stage. There is a series of patent publications which are specifically directed to such a procedure. EP 0 01 3 665 and EP 0 061 785 describe the single-stage reductive amination of triacetone amine derivatives with di- or higher polyamines in the presence of methanol using platinum on carbon as catalyst. However, in these methods, concentrated sulfuric acid must be used conjointly as co-catalyst.

DE 26 21 870 describes the reductive amination of alkylpiperidones with methylamine or ammonia in methanol, using 15% Raney nickel as catalyst. EP 0 208 455 discloses the single-stage reductive amination of piperidones with alkylamines or alkylenediamines in an alcohol or glycol and in the presence of cobalt, nickel or platinum catalysts. To decrease the flammability, the solvent used is alcohol/water mixtures having a water content of at least 10% by volume. A similar process using palladium as catalyst is described in EP 0 202 001.

EP 0 081 688 and 0 045 048 and JP 76-009486 describe the single-stage reductive amination of piperidones with dialkylamines or trialkylamines in methanol and in the presence of platinum on carbon as catalyst. EP 0 302 020 discloses the single-stage reductive amination of piperidones with alkylamines without solvent, with up to 10% by weight of water being permitted to remain in the reaction mixture.

Most recently, the development is again directed towards the two-stage processes, because development of the actually preferred single-stage processes to complete satisfaction has not yet been successful. For example, EP 0 508940 describes the two-stage reductive amination of piperidones with diamines. In the first stage, the Schiff's base is generated in the absence of a solvent by distilling off the water of reaction. In the second stage, the anhydrous Schiff's base is hydrogenated on palladium, platinum or Raney nickel. An apparent advantage of the process, it is that because it is a two-stage procedure, a Schiff's base of high purity is generated, a result of which is that the subsequent hydrogenation proceeds more selectively and more rapidly than hitherto, even at elevated temperatures.

The processes of the prior art which, without exception, are batchwise processes, have a number of disadvantages. For one thing, the constant start-up and shut-down of the individual batches is associated with a comparatively high labor requirement and leads additionally to low space-time yields and increased energy consumption. Most of the known processes use flammable solvents, which, on the one hand, further decrease the space/time yields, and on the other hand, necessitate higher expenditure for fire precautions and additionally also further increases in material costs. In addition, the finely particulate hydrogenation catalysts are generally pyrophoric and, therefore, even in the absence of flammable solvents, can only be handled with safety precautions, both during the initial charging, and during later batches. In addition, catalysts of this type, as is stated in EP 0 508 940, are sensitive to catalyst poisons and cannot be regenerated simply. Noble metal catalysts must be reprocessed just for reasons of cost. The disposal of nickel and cobalt catalysts is problematic, because of their toxicological properties.

The conversion rate of the starting materials and the selectivity of the formation of the desired N-monosubstituted 4-aminopiperidine leave something to be desired, in particular in the case of the single-stage procedure, which would actually be preferred for technical reasons. This is understandable, because, in the single-stage procedure, hydrogenation of the N-substituted 4-aminopiperidones to give the corresponding 4-aminopiperidone can take place, which hydrogenation is greatly reduced in the two-stage procedure, and, in addition, other byproducts form. However, the solvent-free crude reaction mixtures seldom contain more than 90% by weight of the target product, whose content can only be increased to 92–93% by weight by conjoint use of a co-catalyst, which then in any case must be removed again. These are contents which can be achieved by the more complex two-stage process, even without a co-catalyst, by removing the water of reaction in the first stage.

Because of the relatively low contents of the desired product in the crude reaction mixtures, it is difficult to prepare a sufficiently pure N-monosubstituted 4-aminopiperidine. According to DE 41 20 550, a single-stage batch process produces a crude reaction mixture containing 93% by weight of desired product, 0.8% by weight of starting ketone, which has an APHA value (in 10% strength by weight toluene solution) of 400 and, by conventional distillation (boiling point 180–190° C., about 1 mbar) of the reaction mixture, a light solid containing>99% by weight of desired product, 100 ppm of starting ketone which has an APHA value of 100. However, the product is not storage-stable, but after 3 months at 60° C., shows an APHA value of>1,000. Products having adequate storage stability are only obtained by a batchwise crystallization from a ketone solvent. Although the analytical data of the crystals do not differ from those of the distillate, the APHA value is only ≦30 and increases after three months at 60° C. to only ≦100. It is obvious that this additional purification step is complex and undesirable.

The only known continuous process for preparing 4-alkylaminopiperidines is the reductive alkylation of 4-aminopiperidines with the corresponding alkanols as described in EP 0 128 285. The process operates with high amine excess, and only about 10% by weight of the desired product is present in the material discharged from the reaction, so that in order to increase the degree of conversion, the unreacted starting material must be separated and recycled in complex additional steps. A need, therefore, continues to exist for an effective single stage, continuous process of preparing N-monosubstituted-4-aminopiperidines by reaction of 4-oxopiperidine with a primary amine.

SUMMARY OF THE INVENTION

Accordingly, one object of the present invention is to provide a single-stage, effective continuous method of preparing N-monosubstituted-4-aminopiperidines by the reaction of a primary amine with 4-oxopiperidines.

Briefly, this object and other objects of the present invention as hereinafter will become more readily apparent can be attained by a process for preparing N-monosubstituted-4-aminopiperidine in a single stage reaction by continuously passing a 4-oxopiperidine and a primary amine over a metal hydrogenation catalyst under a hydrogen partial pressure of 1–500 bar at a LHSV of up to 1 $hr^{-1}$.

DETAILED DESCRIPTION OF THE PREFERRED EMBODIMENTS

The process according to the invention is associated with a number of advantages which the processes of the prior art do not have in this combination:

(i) The complex start-up and shut-down of individual batches is unnecessary.

(ii) The space-time yields are improved by this means so greatly that values of up to 1 $hr^{-1}$ are achieved for the LHSV (liquid hourly space velocity).

(iii) The supported catalysts preferably used containing metals of Group VIII of the Periodic Table of the Elements can be set so that they are not pyrophoric and they are, therefore, readily handleable.

(iv) The supported catalysts are versatile and are outstandingly suitable for the most varied starting material systems (4-oxopiperidine/primary amine).

(v) The supported catalysts have very long service lives, so that the costs of procurement, installation and removal, disposal or reprocessing are considerably decreased.

(vi) Solvent losses and environmental pollution by solvents, as are associated with recycling catalysts in the case of batch processes, are avoided.

(vii) The supported catalysts and, thus, the process are, therefore, simultaneously economically and ecologically advantageous.

(viii) The process, in comparison to previously known processes, is distinguished by higher degrees of conversion, which can be>99%.

(ix) Because of the comparatively low thermal loading, secondary reactions and decomposition reactions are suppressed, so that a higher selectivity results, which can likewise be>99%, based on the 4-oxo-piperidine.

(x) These favorable results are achieved in a continuous process having only one reaction stage without separate preparation of the Schiff's base in advance, without co-catalyst and without use of solvent, (xi) Surprisingly, the crude reaction mixtures may be purified by conventional distillation without complex crystallization to give storage-stable products.

Preferred N-monosubstituted 4-aminopiperidines of the formula:

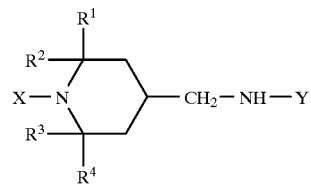

I are prepared by continuously reacting a 4-oxopiperidine of the formula:

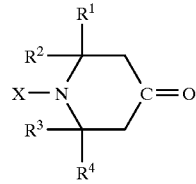

II with a primary amine of the formula:

$Y-NH_2$         III and hydrogen under hydrogenation conditions.

Other preferred N-monosubstituted 4-aminopiperidines of the formula:

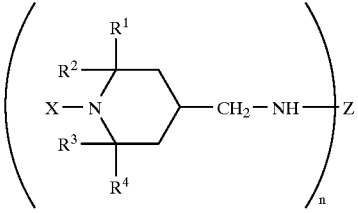

IV are obtained by continuously reacting a 4-oxopiperidine of the formula:

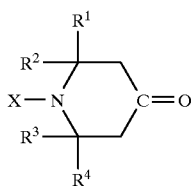

is a polyamine of the formula:

as primary amine and with hydrogen under hydrogenation conditions.

In formula I to V, $R^1$, $R^2$, $R^3$ and $R^4$ can be identical or different and denote hydrogen or a hydrocarbon radical having 1–4 carbon atoms, advantageously a methyl radical; X represents hydrogen; a hydroxyl group; a hydrocarbon radical having up to 18 carbon atoms, advantageously an alkyl radical having 1–12 carbon atoms, a cycloalkyl radical having 3–12 carbon atoms, an aralkyl radical having 7–10 carbon atoms or an alkylaryl radical having 7–10 carbon atoms; an acyl radical having 2–10 carbon atoms; an amino or aminoalkyl group having up to 12 carbon atoms which optionally is N,N-dialkylated; or a terminally alkylated alkylene radical of the formula —$(CH_2)_m$—$R^5$, in which $R^5$ denotes a hydroxyl group or an alkoxy radical having 1–6 carbon atoms and m denotes an integer from 1–6; Y denotes a monovalent hydrocarbon radical having from 1–12 carbon atoms which optionally contains ether bridges, (N-alkyl) imino bridges and/or hydroxyl groups and/or optionally aryl substituted; Z denotes an n-valent hydrocarbon radical having 2–12 carbon atoms, which optionally contains either bridges, (N-alkyl)imino bridges and/or hydroxyl groups and/or optionally is aryl substituted; and n represents an integer from 2–4.

The starting materials II are known substances, some of which are available in commercial quantities. Suitable examples of materials include 4-oxopiperidine, 2,6-dimethyl-4-oxopiperidine, 2,6-diethyl-4-oxopiperidine, 2,2,6,6-tetramethyl-4-oxopiperidine, 1-hydroxy-2,2,6,6-tetramethyl-4-oxopiperidine, 1-methyl-2,2,6,6-tetramethyl-4-oxopiperidine, 1-n-hexyl-2,2,6,6-tetramethyl-4-oxopiperidine, 1-acetyl-2,6-dimethyl-4-oxopiperidine, 1-dimethylamino-2,2,6,6-tetramethyl4-oxopiperidine, and 1-dimethylaminoethyl-2,2,6,6-tetramethyl4-oxopiperidine and the like.

Suitable primary amines III include, inter alia, methylamine, ethylamine, n-butylamine, isooctylamine, stearylamine, cyclohexylamine, aniline, toluidine, phenylethylamine, 3-methoxypropylamine, ethoxyethylamine, ethoxyethoxyethylamine, 3-aminopropanol, 2-ethylaminoethylamine, 2-dimethylaminoethylamine, aminoethylmethylethylamine, and the like.

Suitable polyamines V include, for example, ethylenediamine, butylenediamine, hexamethylenediamine, 1,12-diaminododecane, 1,5--diamino-3-oxapentane, 1,5-diamino-3-methyl-3-azapentane, 1,3,5-triamino-n-hexane, and the like.

The 4-oxopiperidines and the primary amines can be used in stoichiometric amounts. In some cases, an excess or deficiency of the 4-oxopiperidine may be advisable, e.g. of 0.5 mol, expediently from 0.01–0.4 mol per equivalent of primary amino groups.

The hydrogenation conditions include the presence of a suitable hydrogenation catalyst. Suitable catalysts which can be used include fixed supported catalysts having one or more metals of Group VIII of the Periodic Table. Suitable supports are all inert materials which withstand the prevailing pressures. Preference is given to supports of aluminum oxide, silicon dioxide and/or silicates. Preferred noble metals of Group VIII are the platinum metals ruthenium, palladium and platinum, and preferred non-noble metals are cobalt and nickel. The amount of the platinum metal in the supported catalysts is up to 20% by weight, advantageously up to 10% by weight, and in particular 0.5–5% by weight. The amount of the non-noble metals is generally in the range up to 40% by weight, advantageously up to 20% by weight, and in particular 3–15% by weight. The metals can be prepared prior to the actual reductive amination reaction by reducing the corresponding oxides or other suitable compounds with hydrogen. Alternatively, this reduction can be combined with the reductive amination. Preferably, the catalysts are prepared in such a manner that the metals are present as relatively coarse particles and are not pyrophoric. Methods suitable for this purpose are known to those of skill in the art of catalysts.

A supported catalyst or a mixture of a plurality of different supported catalysts can be used for a single catalyst bed. Alternatively, the supported catalysts can be used in a plurality of beds having the same or different metals in equal or different concentration. In fact, amounts of catalyst can vary in a concentration gradient, such as a steady increase in catalyst concentration from the start of the reaction zone to its end. However, the concentration can alternatively decrease in the direction of flow of reacting materials. This can be useful, for example in the case of simultaneous use of noble metals and non-noble metals as catalysts. Instead of a plurality of beds of supported catalysts, clearly, a plurality of series-connected reactors can also be used.

It is an advantage of the present process that it can be carried out without solvent. In the event of unfavorable solubility conditions, insufficient compatibility and/or highly different melting points of the starting materials, however, the conjoint use of a solvent can be expedient. In such a case, those solvents are suitable which are recommended for the known batch processes such as alcohols, and aliphatic and aromatic hydrocarbons, if appropriate in a mixture with one another or else with water.

The reductive amination of the invention is generally carried out at hydrogen partial pressures of 1–500 bar, expediently from 20–300 bar. The reaction temperatures are advantageously not above 200° C. and are preferably 80–200° C., in particular 90–190° C. The LHSV are surprisingly high and are, as previously mentioned, up to 1 $h^{-1}$.

The process of the invention can be carried out, for example, as a trickle process, in which the starting materials, which are liquid under the process conditions, are allowed to trickle over the supported catalyst, while the hydrogen is introduced at one or more positions of the reaction zone and is conducted concurrently or countercurrently.

The reaction mixture is expediently purified by distillation under reduced pressure. The distillates conform, as previously stated, with the customary high requirements of purity and storage stability.

Having generally described this invention, a further understanding can be obtained by reference to certain specific examples which are provided herein for purposes of illustration only and are not intended to be limiting unless otherwise specified.

All percentages are by weight, unless stated otherwise.

EXAMPLE 1

A 500 ml trickle-bed reactor was charged with 400 ml of a supported catalyst (0.5% by weight of palladium on aluminum oxide). 2,2,6,6-Tetramethyl-4-oxopiperidine (TAA; triacetone amine) and hexamethylenediame (HDA) in a volumetric ratio of 2.44:1, equivalent to a molar ratio of 2:1, were passed over the catalyst at a hydrogen pressure of 285 bar and a temperature of 110° C. The LHSV (TAA+HDA) was 0.65 $h^{-1}$. 97% Pure TAA (GC analysis) produced a 94% pure N,N'-bis(2,2,6,6-tetramethyl-4-piperidyl)-1,6-hexanediamine, from which a product having a purity>99% with high storage stability was obtained by distillation.

EXAMPLE 2

A 0.5 $m^3$ trickle-bed reactor was charged with 400 l of a supported catalyst (0.5% by weight of palladium on aluminum oxide). 2,2,6,6-Tetra-methyl-4-oxopiperidine (TAA) and hexamethylenediamine (HDA) in a volumetric ratio of 2.44:1, equivalent to a molar ratio of 2:1, were passed over the catalyst at a hydrogen pressure of 285 bar and a temperature of 110° C. The LHSV (TAA+HDA) was 0.60 $h^{-1}$. 97% Pure TAA (GC analysis) produced a 94.5% pure N,N'-bis(2,2,6,6-tetramethyl- 4-piperidyl)-1,6-hexanediamine,from which a product having a purity>99% with high storage stability was obtained by distillation.

EXAMPLE 3

A 500 ml trickle-bed reactor was charged with supported catalyst as in Example 1. TAA and n-butylamine (NBA) in a volumetric ratio of 1.55:1, equivalent to 1 mol of TAA. A 1.1 mol amount of NBA, was passed over the catalyst at a hydrogen pressure of 285 bar at a temperature of 110° C. The LHSV (TAA+NBA) was 0.7 $h^{-1}$. 97% Pure TAA (GC analysis) produced as crude reaction product a 95% pure N-butyl-2,2,6,6-tetramethyl-4-piperidylamine, which was purified by distillation under reduced pressure.

EXAMPLE 4

A 500 ml trickle-bed reactor was charged with supported catalyst as in Example 1. TAA and 3-methoxypropylamine (MPA) in a volumetric ratio of 1.59:1, equivalent to 1 mol of TAA: 1.05 mol of MPA, were passed over the catalyst at a hydrogen pressure of 285 bar at a temperature of 110° C. The LHSV (TAA+MPS) was 0.75 $h^{-1}$. 97% Pure TAA (GC analysis) produced, as a crude reaction product, a 94% pure N-(3-methoxypropyl)-2,2,6,6-tetramethyl-4-piperidylamine,which was purified by distillation under reduced pressure.

EXAMPLE 5

A 500 ml trickle-bed reactor was charged with a supported catalyst as in Example 1. TAA and 3-amino-l-propanol (3-AP) in a volumetric ratio of 2.1:1, equivalent to 1 mol of TAA: 1.05 mol of 3-AP, were passed over the catalyst at a hydrogen pressure of 285 bar at a temperature of 110° C. The LHSV (TAA+3-AP) was 0.9 $h^{-1}$. 97% Pure TAA (GC analysis) produced, as a crude reaction product, a 95% pure N-(3-hydroxypropyl)-2,2,6,6-tetramethyl-4-piperidylamine, which was purified by distillation under reduced pressure.

EXAMPLE 6

A 500 ml trickle-bed reactor was charged with supported catalyst as in Example 1. TAA and 2-ethylaminoethylamine (EAEA) in a volumetric ratio of 1.54:1, equivalent to 1 mol of TAA:1.05 mol of EAEA, were passed over the catalyst at a hydrogen pressure of 285 bar at a temperature of 110° C. The LHSV (TAA+EAEA) was 0.75 $h^{-1}$. 97% Pure TAA (GC analysis) produced, as a crude reaction product, a 94% pure N-(2-ethylaminoethyl)-2,2,6,6-tetramethylpiperidylamine, which was purified by distillation under reduced pressure.

EXAMPLE 7

A 500 ml trickle-bed reactor was charged with supported catalyst as in Example 1. TAA and cyclohexylamine (CHA) in a volumetric ratio of 1.42:1, equivalent to 1 mol of TAA:1.05 mol of CHA, were conducted over the catalyst at a hydrogen pressure of 285 bar at a temperature of 110° C. The LHSV (TAA +CHA) was 0.8 $h^{-1}$. 97% Pure TAA (GC analysis) produced, as a crude reaction product, a 93% pure N-cyclohexyl-2,2,6,6-tetramethylpiperidylamine, which was further purified by distillation under reduced pressure.

EXAMPLE 8

A 500 ml trickle-bed reactor was charged as in Example 1 with a supported catalyst comprising 1% by weight ruthenium on $Al_2O_3$ as support. TAA and 3-amino-1-propanol (3-AP) in a volumetric ratio of 2.1:1, equivalent to 1 mol of TAA:1.05 mol of 3-AP, were passed over the catalyst at a hydrogen pressure of 285 bar at a temperature of 100° C. The LHSV (TAA+3-AP) was 0.6 $h^{-1}$. 97% Pure TAA (GC analysis) produced as crude reaction product, a 93% pure N-(3-hydroxypropyl)-2,2,6,6-tetramethyl-4-piperidylamine, which was further purified by distillation under reduced pressure.

The disclosure of German priority application 197 04 460.3 having a filing date of Feb. 6, 1997 is hereby incorporated by reference into the application obviously, numerous modifications and variations of the present invention are possible in light of the above teachings. It is, therefore, to be understood that within the scope of the appended claims, the invention may be practiced otherwise than as specifically described herein.

What is claimed as new and desired to be secured by Letters Patent of the United States is:

1. A process for preparing an N-monosubstituted 4-aminopiperidine, comprising:

in a single stage, continuously passing a 4-oxopiperidine and a primary amine over a metal hydrogenation catalyst under a hydrogen partial pressure of 1–500 bar at a LHSV of up to 1 $hr^{-1}$.

2. The process of claim 1, wherein the reaction is conducted without a solvent.

3. A process for preparing an N-monosubstituted 4-aminopiperidine of the formula

I

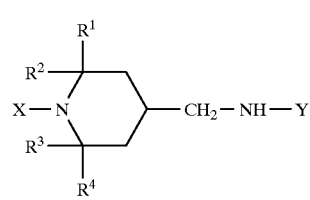

-continued

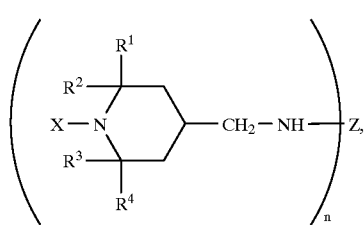

comprising:
in a single stage, continuously passing a 4-oxopiperidine and a primary amine over a metal hydrogenation catalyst under a hydrogen partial pressure of 1–500 bar at a LHSV of up to 1 hr$^{-1}$, wherein the 4-oxopiperidine has the formula:

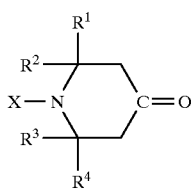

wherein $R^1$, $R^2$, $R^3$ and $R^4$ can be identical or different and denote hydrogen or a $C_{1-4}$ hydrocarbon radical; X represents hydrogen; a hydroxyl group; a $C_{1-18}$ hydrocarbon radical; a $C_{2-10}$ acyl radical; an amino or aminoalkyl group having up to 12 carbon atoms which optionally is N,N-dialkylated; or a terminally substituted alkylene radical of the formula —$(CH_2)_m$—$R^5$, in which $R^5$ denotes a hydroxyl group or a $C_{1-6}$ alkyl radical and m denotes an integer from 1–6; and wherein the primary amine has the formula:

or

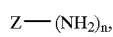

wherein Y denotes a monovalent $C_{1-12}$ hydrocarbon which optionally contains ether bridges, (N-alkyl)imino bridges, hydroxyl groups, or combinations thereof, and is optionally aryl substituted; Z denotes an n-valent $C_{2-12}$ hydrocarbon, which optionally contains ether bridges, (N-alkyl)imino bridges, hydroxyl groups or combinations thereof, and is optionally aryl substituted; and n represents an integer from 2–4.

4. The process of claim 1, wherein the starting materials are passed over a fixed supported catalyst.

5. The process of claim 4, wherein the supported catalyst comprises at least one metal of Group VIII of the Periodic Table.

6. The process of claim 5, wherein the supported catalyst comprises cobalt, nickel, ruthenium, palladium and/or platinum.

7. The process of claim 4, wherein the fixed supported catalyst contains varying amounts of catalytically active metal(s) so as to form a concentration gradient which increases from the initial point of contact of the reaction materials to the finish of contact of said materials with the catalyst.

8. The process of claim 1, wherein the reaction is carried out at 80–200° C.

9. The process of claim 1, wherein said 4-oxopiperidine is 2,6-dimethyl-4-oxopiperidine, 2,6-diethyl-4-oxopiperidine, 2,2,6,6-tetramethyl-4-oxopiperidine, 1-hydroxy-2,2,6,6-tetramethyl-4-oxopiperidine, 1-methyl-2,2,6,6-tetramethyl-4-oxopiperidine, 1-n-hexyl-2,2,6,6-tetramethyl-4-oxopiperidine, 1-acetyl-2,6-dimethyl-4-oxopiperidine, 1-dimethylamino-2,2,6,6-tetramethyl-4-oxopiperidine, and 1-dimethylaminoethyl-2,2,6,6-tetramethyl-4-oxopiperidine..

10. The process of claim 1, wherein the primary amine is methylamine, ethylamine, n-butylamine, isooctylamine, stearylamine, cyclohexylamine, aniline, toluidine, phenylethylamine, 3-methoxypropylamine, ethoxyethylamine, ethoxyethoxyethylamine, 3-aminopropanol, 2-aminoethylmethylethylamine.

11. The process of claim 1, wherein said primary amine is ethylenediamine, butylenediamine, hexamethylenediamine, 1,12-diaminododecane, 1,5-diamino-3-oxapentane, 1,5-diamino-3-methyl-3-azapentane and 1,3,5-triamino-n-hexane.

12. The process of claim 1, wherein the reaction is conducted with an excess of primary amine relative to 4-oxopiperidine.

13. The process of claim 5, wherein said group VIII metal is ruthenium, palladium or platinum.

14. The process of claim 1, wherein the metal hydrogenation catalyst is cobalt or nickel.

15. The process of claim 13, wherein the amount of said platinum metal of a supported catalyst ranges up to 20% by weight.

16. The process of claim 10, wherein said 4-oxopiperidine is 2,6-dimethyl-4-oxopiperidine, 2,6-diethyl-4-oxopiperidine, 2,2,6,6-tetramethyl-4-oxopiperidine, 1-hydroxy-2,2,6,6-tetramethyl-4-oxopiperidine, 1-methyl-2,2,6,6-tetramethyl-4-oxopiperidine, 1-n-hexyl-2,2,6,6-tetramethyl-4-oxopiperidine, 1-acetyl-2,6-dimethyl-4-oxopiperidine, 1-dimethylamino-2,2,6,6-tetramethyl-4-oxopiperidine, and 1-dimethylaminoethyl-2,2,6,6-tetramethyl-4-oxopiperidine.

17. The process of claim 11, wherein said 4-oxopiperidine is 2,6-dimethyl-4-oxopiperidine, 2,6-diethyl-4-oxopiperidine, 2,2,6,6-tetramethyl-4-oxopiperidine, 1-hydroxy-2,2,6,6-tetramethyl-4-oxopiperidine, 1-methyl-2,2,6,6-tetramethyl-4-oxopiperidine, 1-n-hexyl-2,2,6,6-tetramethyl-4-oxopiperidine, 1-acetyl-2,6-dimethyl-4-oxopiperidine, 1-dimethylamino-2,2,6,6-tetramethyl-4-oxopiperidine, and 1-dimethylaminoethyl-2,2,6,6-tetramethyl-4-oxopiperidine.

* * * * *

UNITED STATES PATENT AND TRADEMARK OFFICE
CERTIFICATE OF CORRECTION

PATENT NO. : 5,945,536

DATED : August 31, 1999

INVENTOR(S): Udo JEGELKA, et al.

It is certified that an error appears in the above-identified patent and that said Letters Patent is hereby corrected as shown below:

On the title page, item [73], the assignee's name is misspelled. It should be:

--Huels Aktiengesellschaft--

Signed and Sealed this

Twenty-ninth Day of August, 2000

Attest:

Q. TODD DICKINSON

*Attesting Officer*      *Director of Patents and Trademarks*